United States Patent
Kaneko

(12) 
(10) Patent No.: US 6,586,247 B1
(45) Date of Patent: Jul. 1, 2003

(54) MEDIUM FOR CULTIVATING ANIMAL EMBRYO

(75) Inventor: Satoru Kaneko, Sakato (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/477,807

(22) Filed: Jan. 5, 2000

(30) Foreign Application Priority Data

Jan. 5, 1999 (JP) .......................................... 11-000257

(51) Int. Cl.⁷ ............................. C12N 5/02; C12N 5/06; C12N 5/08
(52) U.S. Cl. ........................................ 435/404; 435/325
(58) Field of Search ................................. 435/404, 325

(56) References Cited

U.S. PATENT DOCUMENTS

| | | | |
|---|---|---|---|
| 3,218,318 A | * 11/1965 | Flynn | 260/243 |
| 4,132,848 A | 1/1979 | Cise et al. | 544/28 |

FOREIGN PATENT DOCUMENTS

| | | |
|---|---|---|
| EP | 0 498 243 A | 8/1992 |
| EP | 0 872 180 A | 10/1998 |
| WO | WO 86/07377 | * 12/1986 |

OTHER PUBLICATIONS

J. Tarin et al.: "Ascorbate–supplemented media in short-term cultures of human embryos"; *Human Reproduction* (OXFORD) 1994, vol. 9, No. 9, pp. 1717–1722 (1994).

J. Conaghan et al.: "Culture of human preimplantation embryos to the blastocyst stage: A comparison of 3 media"; *International Journal of Developmental Biology*; vol. 42, No. 7, pp. 885–893 (1998).

L. Butcher et al.; "Metabolism of pyruvate by the early human embryo"; *Biology of Reproduction*; vol. 58, No. 4, pp. 1054–1056 (1998).

Quinn et al. Fertility and Sterility. Feb. 1984. vol. 41, No. 2, pp. 202–209.*

Quinn et al. Fertility and Sterility. 1985. vol. 44, No. 4, pp. 493–498.*

Freshney R.I. In: "Culture of Animal Cells. A Manual of Basic Technique". 1987. pp. 74–84.*

Waymouth C. In:"Methods for Preparation of Media, Supplements, and Substrata for Serum–Free Aniaml Cell Culture". 1984, pp. 31–68.*

* cited by examiner

*Primary Examiner*—Irene Marx
*Assistant Examiner*—Vera Afremova
(74) *Attorney, Agent, or Firm*—Kubovcik & Kubovcik

(57) ABSTRACT

A medium for cultivating an animal embryo that is capable of readily culturing a fertilized ovum can be provided. A cultivation medium is separated into two parts, i.e., one is a neutral aqueous solution and the other is an acidic aqueous solution. The two parts are mixed before use. The neutral aqueous solution contains a nutrient such as lactic acid or a lactic salt and another inorganic component and an indicator that indicates a state of a development environment with its color, and the acidic aqueous solution contains a nutrient such as pyruvic acid and an antibiotic. The pH change in the medium according to cultivation of animal embryo can be determined by the change of the color of the indicator.

1 Claim, No Drawings

MEDIUM FOR CULTIVATING ANIMAL EMBRYO

FIELD OF THE INVENTION

The present invention relates to a medium for cultivating an animal embryo, and more specifically, to a medium for cultivating an animal embryo in which an externally fertilized ovum is cultivated up to a condition implantable into a uterus cavity.

BACKGROUND OF THE INVENTION

A medium for a cultivating cell culture is a medium for supplying nutrients essential for a cell derived from a living body or the like to exist, maintain its function, or proliferate, and for diffusing and removing waste products. As to the medium, a medium containing generally amino acids, vitamins, glucose, trace metals, and others is used with additives such as serum. However, an animal embryo may less use glucose in an early state of development, and rather need pyruvic acid and lactic acid. Therefore, an externally fertilizing medium (HTF medium) in which pyruvic acid and lactic acid are added into an Earle solution, a buffer solution as a base component, can be used in order to cultivate an animal embryo. Also used is a medium in which antibotics such as Penicillin G or streptomycin sulfate and serum are added to a minimum essential nutrient medium (α-MEM medium) containing an Earle solution as a base component.

However, problematic issues as described below often arise when an animal embryo, especially a fertilized ovum is cultivated using the above mentioned medium added with pyruvic acid, lactic acid and antibiotics.

Semen can be purified by a method such as centrifugation, or swimming up, but the sperm may be contaminated with bacterium which usually exist around an external urethral orifice at the time of ejaculation and may be not aseptic. Therefore, an antibiotic such as Penicillin G or Streptomycin sulfate can be added into a conventional medium, but these antibiotics can not maintain the antibacterial activity because they are easily hydrolyzed in an aqueous solution.

Pyruvic acid is unstable in neutral aqueous solution so that the initially added concentration can not be maintained in a commercially available medium of pH of 7.2 to 7.3.

As an antioxidant such as superoxide dismutase that contributes resistance against oxygen can not be induced, an undifferentiated early embryo may be effected with oxygen.

SUMMARY OF THE INVENTION

As a result of intensive research to solve the above-described problems, the inventors of the present invention have completed a medium for cultivating an animal embryo with which the development state of an animal embryo can be easily determined by observing the color change of an indicator according to pH change in the medium. The pH in the medium changes as the animal embryo cultivation progresses. The medium for cultivating an animal embryo comprises two separate parts, one of which is a neutral aqueous solution containing a nutrient and a color indicator which shows the state of a development environment dissolved therein, the other is an acidic aqueous solution containing a nutrient and an antibiotic dissolved therein.

That is, the present invention relates to a medium for cultivating an animal embryo, which comprises the following aqueous solutions (A) and (B) which are mixed before use:

(A) a neutral aqueous solution containing a nutrient that is stable in an approximately neutral condition and an indicator that indicates the state of a development environment with a change in color; and (B) an acidic aqueous solution containing a nutrient that is stable in an acidic condition and an antibacterial agent that suppresses the development of bacterium.

DESCRIPTION OF THE PREFERRED EMBODIMENTS

Examples of the nutrient stable in the approximately neutral condition in an aqueous solution (A) of the present invention include basic components such as lactic acid or lactic salt and another inorganic component or components.

As for the aqueous solution (A), there are exemplified an aqueous solution of lactic salt, for example, sodium lactate. The content of sodium lactate in the aqueous solution (A) is 1.0 to 2.0 ml/l, preferably, 1.5 to 2.0 ml/l.

Inorganic components other than lactic acid are sodium chloride, potassium chloride, calcium chloride, magnesium chloride, magnesium sulfate, and sodium bicarbonate which include a basic component such as sodium, potassium, calcium, magnesium, and chlorine. The content of the inorganic components is 6.0 to 11.0 g/l, preferably, 8.0 to 9.5 g/l in the aqueous solution (A).

In addition, a trace of inorganic components, for example, iron can be contained.

Carbon sources such as glucose, nitrogen sources such as amino acid and hormones such as estrogen or androgen complying with the metabolic capability of the organism may also be contained in aqueous solution (A).

Further, in the aqueous solution (A) of the present invention, an indicator that makes it possible to perceive a state of a development environment externally is a pH indicator that indicates the pH change caused by cultivation of the animal embryo as a change in color, such as phenol red (pKa=7.9), bromotymol blue (pKa=7.1), and o-cresol blue (pKa=8.2). The pH indicator may be any one that can change the color when the aqueous solution (A) converts from approximately neutral to an acidic condition. The content of the indicator is 1.0 to 3.0 mg/l, preferably, 1.0 to 2.0 mg/l in the aqueous solution (A).

The medium is exchanged when the development environment becomes inappropriate for the animal embryo development.

An antibacterial agent contained in an aqueous solution (B) of the present invention and which suppresses the development of bacterium is exemplified by fosfomycin, cephem antibiotics (such as cepharothin), β-lactam antibiotics, aminoglycoside antibiotics, tetracycline antibiotics, macrolide antibiotics, peptide antibiotics, nucleoside antibiotics, polyene antibiotics and the like. At least one of these antibiotics may be used. Of these, fosfomycin and cephem antibiotics (such as cepharothin) that prevent biosynthesis of peptide glycan on the bacteria cell walls are particularly preferable. The content of the antibacterial agent is 0.5 to 3.0 g/l, preferably, 1.0 to 2.0 g/l in the aqueous solution (B).

Further, examples of the nutrients that are stable in an acidic condition in the aqueous solution (B) of the present invention include pyruvic acid and a substance that can promote metabolism from lactic acid to pyruvic acid by an animal embryo, for example, coenzymes such as nicotinamide adenine dinucleotide (NAD). The content of pyruvic acid is 1.0 to 3.0 ml/l, preferably, 1.5 to 3.0 ml/l, in the aqueous solution (B). The content of the metabolic promoting substance is 0.03 to 0.07 g/l, preferably, 0.04 to 0.06 g/l in the aqueous solution (B).

In addition, composite antioxidants may be included in the aqueous solution (B) of the present invention. These include combinations of antioxidants which contribute oxygenic resistance in early embryo such as glutathione, N-acetyl cysteine, cysteine, ascorbic acid (vitamin C), α-tocopherol, uric acid, pyruvic acid, glucose, albumin, and ferritin. The composite antioxidant uses in combination at least two of these antioxidants. If the antioxidant comprises only one kind, the efficiency is decreased by oxidation of the antioxidant that contributes resistance against oxygen in early embryo.

Especially, a composite antioxidant that contributes oxygenic resistance in early embryo is preferably glutathione, and cysteine or ascorbic acid (vitamin C) which can prevent oxidation of glutathione by a difference of redox potential. The content of the composite antioxidant is 7.0 to 15.0 g/l, preferably, 10.0 to 12.0 g/l in the aqueous solution (B).

On the occasion of cultivating the animal embryo, the above aqueous solution (A) and aqueous solution (B) are mixed into a medium of the present invention so as to be used. The pH value of aqueous solution (A) is 7.0 to 7.5. A buffer like HEPES may be added into the solution. If the pH value of the aqueous solution is below 7.0, the pH when it is mixed becomes inappropriate for cultivation. On the other hand, if the pH value of aqueous solution (A) is above 7.5, the mixture is also inappropriate for cultivation.

The pH value of the aqueous solution (B) is 4.0 to 5.5. To adjust the pH value in the aqueous solution, NaOH may be added. If the pH value is below 4.0 or above 5.5, the components will be decomposed.

The mixing ratio of the aqueous solution (A) and the aqueous solution (B), that is, (A):(B) is 100:1 to 50:1 (volume ratio).

An example of the composition of each component in the present medium is described as follows.

Aqueous solution (A): an aqueous solution containing all of the following components and adjusted to have a pH of 7.0 to 7.5.

| | |
|---|---|
| sodium lactate | 1.0 to 2.0 ml |
| sodium chloride | 5.0 to 7.0 g |
| potassium chloride | 0.3 to 0.5 g |
| calcium chloride.2H$_2$O | 0.1 to 0.4 g |
| magnesium sulfate.7H$_2$O | 0.03 to 0.1 g |
| Phenol Red | 1.0 to 3.0 mg |
| sodium bicarbonate | 1.5 to 3.0 g |
| HEPES | 2.0 to 5.0 g |
| glucose | 0.1 to 0.8 g |
| pure water | |
| Total | 1,000 ml |

Aqueous solution (B): an aqueous solution containing all of the following components and adjusted to have a pH of 4.0 to 5.5.

| | |
|---|---|
| pyruvic acid | 1.0 to 3.0 ml |
| glutathione | 0.3 to 0.8 g |
| L-cysteine hydrochloride | 4.0 to 7.0 g |
| ascorbic acid | 3.0 to 7.0 g |
| NAD | 0.03 to 0.07 g |
| cepharothin | 0.3 to 0.7 g |
| fosfomycin | 0.5 to 1.5 g |
| pure water | |
| Total | 1,000 ml |

Next, the present invention will be illustrated in detail with an example.

EXAMPLE 1

A medium containing 25 ml of the aqueous solution (A), 0.3 ml of aqueous solution (B) described below and 5 ml serum which are mixed before use was placed in a culture vessel. 5 to 8 human early embryos were collected from each of 37 women and were disseminated in the medium in 37 vessels. Then, static cultivation was carried out for 40 to 70 hours under an atmosphere of 5% $O_2$, 5% $CO_2$ and 90% $N_2$ at a temperature of 37° C. After cultivation, human early embryos that developed 4 to 8 segments were recognized under a microscope, and three of them were implanted into a patient, and then diagnosis of pregnancy was carried out using a pregnant diagnostic agent and supersonic imaging after one month. The results are shown in Table 1.

For comparison, human early embryos were similarly cultivated in a commercially available HTF medium (manufactured by GIBCO) and diagnosis was conducted to determine whether a patient is pregnant or not.

Aqueous solution (A): an aqueous solution containing the following components and adjusted to have a pH of 7.4,

| | |
|---|---|
| sodium lactate | 1.73 ml |
| sodium chloride | 6.02 g |
| potassium chloride | 0.35 g |
| calcium chloride | 0.295 g |
| magnesium sulfate | 0.075 g |
| Phenol Red | 1.5 mg |
| sodium bicarbonate | 2.10 g |
| HEPES | 3.34 g |
| glucose | 0.1 g |
| pure water | |
| Total | 1000 ml |

Aqueous solution (B): an aqueous solution containing the following components and adjusted to have a pH of 4.5,

| | |
|---|---|
| pyruvic acid | 2.03 ml |
| glutathione | 0.50 g |
| L-cysteine hydrochloride | 5.40 g |
| ascorbic acid | 5.0 g |
| NAD | 0.05 g |
| cepharothin | 0.50 g |
| fosfomycin | 1.00 g |
| pure water | |
| Total | 1,000 ml |

TABLE 1

| Kind of medium for cultivating animal embryo | Number of samples | Number of pregnant patients | ratio (%) of pregnant patients |
|---|---|---|---|
| commercially available HTF medium | 42 cases | 11 cases | 26.2 |
| medium in the present invention | 37 cases | 12 cases | 32.4 |

As apparent from the table 1, the medium for cultivating an animal embryo of the present invention shows a higher pregnancy ratio in the excellent development of human early embryo as compared with a commercially available HTF medium.

The medium for cultivating an animal embryo of the present invention can prevent carrion caused by bacteria contamination by means of an antibacterial agent and is capable of good development of an animal embryo by nutrients contained therein.

What is claimed is:

1. A medium for cultivating an animal embryo or fertilized ovum, which consists essentially of the following aqueous solutions (A) and (B) which are mixed before use:

(A) 50 to 100 parts by volume of a neutral aqueous solution having a pH of 7.0 to 7.5 and containing the following components:

| | |
    |---|---|
    | sodium lactate | 1.0 to 2.0 ml |
    | sodium chloride | 5.0 to 7.0 g |
    | potassium chloride | 0.3 to 0.5 g |
    | calcium chloride.2H$_2$O | 0.1 to 0.4 g |
    | magnesium sulfate.7H$_2$O | 0.03 to 0.1 g |
    | Phenol Red | 1.0 to 3.0 mg |
    | sodium bicarbonate | 1.5 to 3.0 g |
    | HEPES | 2.0 to 5.0 g |
    | glucose | 0.1 to 0.8 g; | and (B) 1 part by volume of an acidic aqueous solution having a pH of 4.0 to 5.5 and containing the following components:

| | |
    |---|---|
    | pyruvic acid | 1.0 to 3.0 ml |
    | glutathione | 0.3 to 0.8 g |
    | L-cysteine hydrochloride | 4.0 to 7.0 g |
    | ascorbic acid | 3.0 to 7.0 g |
    | NAD | 0.03 to 0.07 g |
    | cepharothin | 0.3 to 0.7 g |
    | fosfomycin | 0.5 to 1.5 g. |

* * * * *